(12) United States Patent
Damien et al.

(10) Patent No.: US 7,510,725 B2
(45) Date of Patent: *Mar. 31, 2009

(54) PROCESS FOR PRODUCING A DURA SUBSTITUTE

(75) Inventors: Christopher James Damien, Newtown, PA (US); Heather Ann Beam, Penndel, PA (US); Gerry Ann Oster, Langhorne, PA (US); Frederic S. Wright, Ardmore, PA (US); Gonzalo Serafica, Langhorne, PA (US)

(73) Assignee: Synthes USA, LLC, West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/103,079

(22) Filed: Apr. 15, 2008

(65) Prior Publication Data

US 2008/0213844 A1     Sep. 4, 2008

Related U.S. Application Data

(63) Continuation of application No. 10/923,084, filed on Aug. 23, 2004, now Pat. No. 7,374,775.

(60) Provisional application No. 60/497,019, filed on Aug. 22, 2003.

(51) Int. Cl.
*A61F 2/00*     (2006.01)
*C12P 1/04*     (2006.01)
*C12P 19/04*    (2006.01)

(52) U.S. Cl. .................... 424/424; 424/428; 424/488; 435/41

(58) Field of Classification Search .............. None
See application file for complete search history.

(56) References Cited

U.S. PATENT DOCUMENTS

| | | | |
|---|---|---|---|
| 3,872,862 A | 3/1975 | Hume | |
| 4,655,756 A | 4/1987 | Fawkes | |
| 4,703,108 A | 10/1987 | Silver et al. | |
| 4,942,128 A | 7/1990 | Brown, Jr. | |
| 4,950,263 A | 8/1990 | Lewis | |
| 5,013,366 A | 5/1991 | Jackson et al. | |
| 5,580,348 A | 12/1996 | Blaney et al. | |
| 5,772,646 A | 6/1998 | Blaney et al. | |
| 5,942,218 A | 8/1999 | Kirschner et al. | |
| 6,320,093 B1 | 11/2001 | Augustine et al. | |
| 6,369,289 B1 | 4/2002 | Orr, III | |
| 6,599,518 B2 | 7/2003 | Oster et al. | |
| 7,374,775 B2 | 5/2008 | Damien et al. | |
| 2002/0107223 A1 | 8/2002 | Oster et al. | |

OTHER PUBLICATIONS

Mello, L.R. et al "Duraplasty with biosynthetic cellulose: An experimental study" Journal of Neurosurgery,1997, 86(1),pp. 143-150.*
Heslot, H., Biochemie, 1998, 80, 19-31.
"Ethanol", Material Safety Data Sheet, section 9—Physical/Chemical Properties, accessed Apr. 30, 2007 <http://www.sigma-aldrich.com>, 6 pages.
"Water", Material Safety Data Sheet, section 9—Physical/Chemical Properties, accessed Apr. 30, 2007 <http://www.sigma-aldrich.com>, 4 pages.
Redacted agreement, Exhibit A to Rule 132 Declaration of Russel Hoon, 2005, 33 pages.
Jun. 22, 1998 510(k) approval No. K974251 for X-Cell Wound Dressing (printed out from FDA web site), 4 pages.

* cited by examiner

*Primary Examiner*—Sandra Saucier
*Assistant Examiner*—Aaron J Kosar
(74) *Attorney, Agent, or Firm*—Woodcock Washburn LLP

(57) ABSTRACT

The invention relates to dura substitutes to be used as prostheses for dural defects in the field of neurosurgery and processes for producing the same. The present invention provides artificial dura mater materials comprising sheets of microbial-derived polysaccharide processed to have the necessary strength characteristics, conformability and physical properties.

13 Claims, 3 Drawing Sheets

PROCESS FOR PRODUCING A DURA SUBSTITUTE

CROSS-REFERENCE TO RELATED APPLICATIONS

This application is a continuation of U.S. application Ser. No. 10/923,084 filed Aug. 23, 2004, which claims benefit U.S. Provisional Application Ser. No. 60/497,019, filed Aug. 22, 2003, which is hereby incorporated by reference in its entirety.

FIELD OF THE INVENTION

The present embodiments of the invention relate to dura substitutes, in particular, to be used as prostheses for dural defects in the field of neurosurgery and processes for producing the same. Moreover, the embodiments of the present invention provide artificial dura mater comprising a sheet of microbial-derived polysaccharide having the necessary strength characteristics and a process for producing an artificial dura mater characterized by producing the polysaccharide sheet via fermentation, removing any contaminants in the sheet via a chemical wash and dehydrating the resulting sheet prior to final packaging.

BACKGROUND OF THE INVENTION

Dura mater is the outermost membrane that comprises the meningeal membrane between the cranial bones and brain. Its function is to protect the brain and inhibit leakage of cerebrospinal fluid. Dura mater also covers the spinal cord providing a similar function. In the field of neurosurgery, any defect or contracture of the dura mater has to be repaired. Various materials have been used for this purpose.

Human-derived dura mater allograft from donors was the most utilized material for repairing the dura mater. However, the incidence of transmission of the agent that causes Creutzfeldt—Jakob disease (CJD) through the use of the human cadaver dura mater has greatly reduced its use. In addition, human dura mater allograft has several disadvantages including low homogeneity and a limited supply.

Other materials have been used as dura substitutes including synthetic polymers such as silicone or ePTFE (expanded polytetrafluoroethylene) and naturally occurring polymers such as collagen. Each of these materials has its own drawbacks. For example, silicone has been reported to predispose patients to meningorrhagia. Silicone acts as a chronic stimulant for the surrounding tissue causing hypertrophy of the granulation tissue. Similar non-biodegradable synthetic materials, such as ePTFE, have been developed but have not become popular because a similar chronic foreign body response develops with their use and their handling characteristics are poor. Other synthetic materials used in bio-absorbable sutures such as polylactides and polyglycolides (PLA/PGA) as described in U.S. Pat. No. 5,861,034 have been developed. However, these materials have yet to show improved clinical performance over earlier unsuccessful synthetic predecessors.

Various naturally occurring biodegradable materials have been investigated. For example, gelatin was one of the earliest biomaterials investigated. Gelatin did not gain acceptance because it had insufficient suture strength for integral use with the internal dura mater. Similarly, other collagenous biomaterials that also lack the necessary suture strength have been described in U.S. Pat. No. 5,997,895. These materials have been commercially available and have gained widespread use as onlay materials. However, when hydrated, these materials convert to a gelatinous mass that has no structural integrity. Thus, there is still a need for a dura substitute that possesses the desirable physical properties such as strength and conformability and in some cases, suturability, and one that has minimal foreign body response.

Microbial cellulose has been suggested for some medical uses. For example, the use of microbial derived cellulose in the medical industry as liquid loaded pads (U.S. Pat. No. 4,788,146), wound dressings (U.S. Pat. No. 5,846,213) and other topical applications (U.S. Pat. No. 4,912,049). Mello et al., (Mello, L. R., et al., *Duraplasty with Biosynthetic Cellulose: An Experimental Study. Journal of Neurosurgery*, V. 86, 143-150 (1997)) published the use of biosynthetic cellulose similar to the one described in (U.S. Pat. No. 4,912,049) as a duraplasty material in an experimental animal study. Their results showed that the dried form of the microbial derived cellulose was adequate as a dural substitute. However, the material described by Mello et al. does not undergo a depyrogenation step and the material is fully dried while being stretched as described in U.S. Pat. No. 4,912,049.

In contrast, the instant invention provides a non-pyrogenic implantable material and uses either a mechanical or a thermal dehydration method to partially dehydrate the surgical mesh without drying, resulting in two materials that have unique characteristics. Further, these materials can be dried using a supercritical carbon dioxide technology so as to provide a dried product. This processing endows the invention with superior conformability and absorption properties not available in previously described cellulosic materials including the air-dried cellulose of Mello et al.

OBJECTIVES OF THE INVENTION

An embodiment of the current invention is to provide microbially-derived cellulose processed with a unique method of partial water removal using mechanical and/or thermal dehydration methods or almost total water removal using the same methods followed by supercritical fluid drying. These new processes of partial dehydration and drying result in dehydration of the cellulose sheets that can be reconstituted to obtain the desirable moisture level for an ideal dura substitute.

Another embodiment of the present invention is to provide microbially-derived cellulose that has improved physical characteristics, such as non-leakage, conformability, suture strength, and a process for producing the same.

SUMMARY OF THE INVENTION

Figure 1:
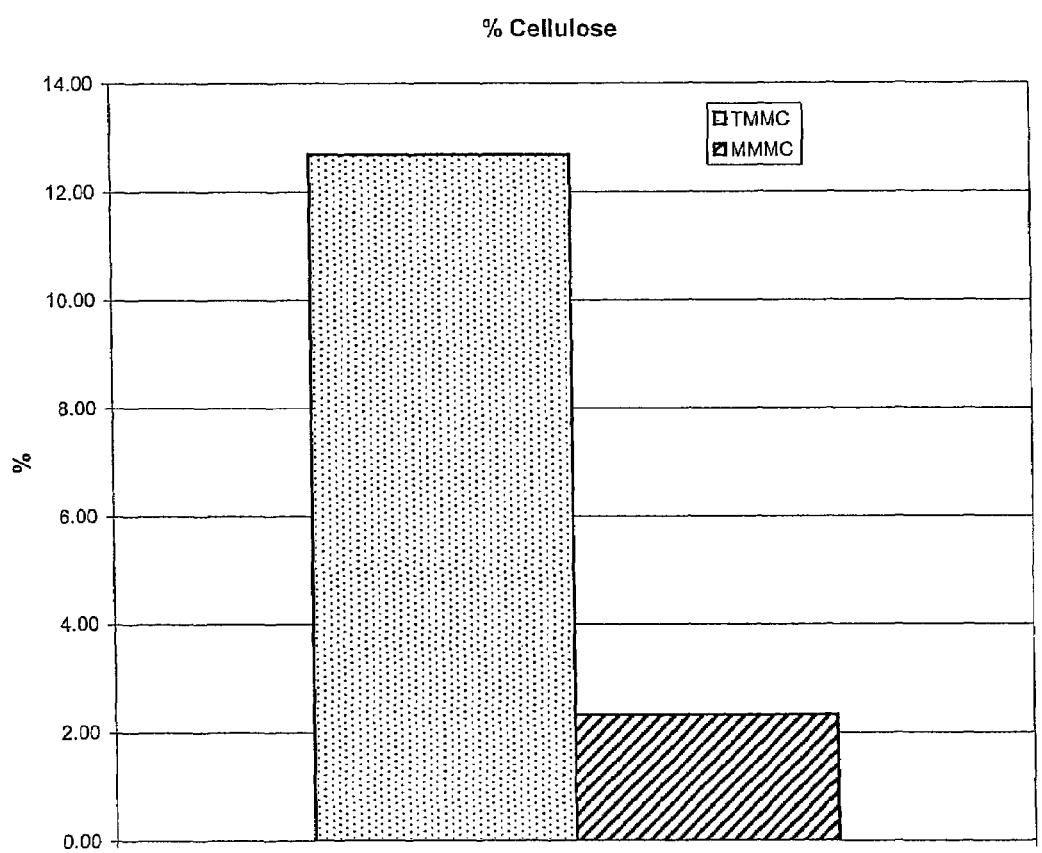
FIG. 1 shows the difference in cellulose content of thermally modified microbial-derived cellulose (TMMC) compared to mechanically modified microbial cellulose (MMMC).

An embodiment of the present invention provides an artificial dura mater that includes a microbial-derived polysaccharide which has desired strength and conformability characteristics and is non-pyrogenic. The polysaccharide described in this invention may be cellulose produced by *Acetobacter xylinum*. Another embodiment of the present invention discloses a process for producing an artificial dura mater which may include the step of producing the polysaccharide via fermentation which may occur under static conditions and progress for about 5 days to about 30 days. Then the process may include removing any contaminants via caustic chemical washing followed by rinsing with water. In one embodiment, the process may include partially dehydrating the resulting microbial cellulose to obtain the desired final composition where the partial dehydration may be done by mechanical modification or by thermal modification where a temperature is maintained below 0° C. for a determined period of time before increasing above freezing. For additional embodiments, the material can be further dried using supercritical carbon dioxide technology.

For the onlay dura substitute, a typical cellulose content of about 2% to about 10% may be desirable and with a preferred content that may include about 2% to about 3%. For a suturable dura substitute, a cellulose content of about 5% to about 21% is preferred, although one that is greater than 95% might be applicable as in the case of a completely dehydrated material.

Furthermore, an embodiment of the invention provides a method for treating a dural defect which may include suturing together the residual native dura mater and an artificial dura mater to cover the dural defect section or may include placing the artificial dura mater over the brain as an onlay.

An artificial dura mater as embodied by this invention may have the desired strength characteristics to act as prosthesis for dural defects with a tensile strength of about 0.6 MPa to about 16 MPa. A preferred embodiment of the invention may have a tensile strength of about 1 MPa to about 4 MPa for the onlay materials, and about 2 MPa to about 16 MPa is preferred for the sutureable version of the invention.

In addition, the elongation for these particular materials may be about 17% to about 40%. This elongation value seems to provide sufficient extensibility when subjected to a suturing under tension. The material has also been found to have minimal leakage of fluid when pressure is applied thereto. These implants have also been show to have an average burst strength value of about 20N to about 30N.

The suture strength may be greater than about 0.1 MPa, preferably about 0.6 MPa.

In the artificial dura mater of the invention, an average stiffness value of about 0.8N to about 2.7N offers the artificial dura mater less rigidity so as not to damage the brain surface. The artificial dura mater was also found to be flexible and easy to handle.

According to the embodiments of the invention as explained above, there can be provided an artificial dura mater improved of its qualities such as leakage and suture strength and a process for producing the same.

DETAILED DESCRIPTION OF THE INVENTION

The following detailed description illustrates specific embodiments of the invention, but is not meant to limit the scope of the invention, which is defined by the claims.

Unless otherwise specified, the words "a" or "an" as used herein mean "one or more".

Raw Material Production of Dura Substitutes Via Fermentation

In preparing the microbial cellulose of the invention, microorganisms such as *Acetobacter xylinum* are cultured in a bioreactor containing a liquid nutrient medium at 30° C. at an initial pH of about 3 to about 6. The medium is based on sucrose or other carbohydrates. Preferably, efficient cellulose production is achieved using sucrose as a carbon source, ammonium salts as a nitrogen source, and corn steep liquor as nutrient source.

Suitable bioreactors are selected which minimize evaporation and provide adequate oxygen-limiting conditions. The bioreactor may be composed of a clean, dry plastic box fitted with an airtight or limited gas-permeable cover. An aeration port is added to regulate the oxygen-limiting conditions. Dimensions of the bioreactor can vary in configuration depending on the desired shape, size and thickness of the cellulose film being produced. The fermentation process under static conditions is allowed to progress over for a period of about 5 days to about 30 days, during which the bacteria in the culture medium produce an intact cellulose sheet containing the microorganisms. Depending on the desired thickness, which corresponds to a certain cellulose content per unit area, the fermentation is stopped and the sheet is removed from the bioreactor. The excess medium contained in the pellicle is then removed by standard separation techniques such as compression or centrifugation prior to chemical cleaning.

Removal of Cells and Excess Medium

The chemical processing renders the microbial cellulose nonpyrogenic and is done in the following manner. The cellulose sheet is subjected to a series of caustic chemical wash steps to convert the raw cellulose film into a medical grade and non-pyrogenic material, followed by rinsing with filtered water.

Purification processes using various exposure times, concentrations and temperatures were conducted on the raw fermentation product. Processing times of about 1 to about 4 hours have been studied in conjunction with temperature variations of about 30° C. to about 100° C. to optimize the process. The resulting films from each of the different operating conditions were tested for their respective pyrogen levels and physical characteristics. The optimization was performed so that conditions yielded a nonpyrogenic product in the least amount of time and lowest chemical concentration. The time involved in this process can be as much as 4 hours at about 50 to about 90° C.; preferably the time involved is about 1 to about 2 hours at about 60° C. to about 80° C. The amount of cellular debris left in the cellulose pad after processing may be measured by *Limulus Amebocyte* Lysate (LAL) test as outlined by the U.S. Food and Drug Administration (FDA) in 21 CFR10.90. The instant cleaning process outlined above provided a nonpyrogenic cellulose pad (<0.06 EU/ml) that is required by the FDA for dura substitute materials.

Partial Dehydration by Mechanical Means

Following the cleaning process described above, the cellulose pellicle is mechanically compressed to the predetermined weight desired for form, fit and function as a dura substitute. The original fill volume and the compression steps are integral to the present invention to attain the desired density that affects the strength, integrity, and function of the cellulose. Partially dehydrated samples are packaged in a single- or double-pouch system in preparation for sterilization. Samples are tested for cellulose content, endotoxin, and mechanical strength.

Partial Dehydration Process Using Thermal Modification

Further processing of the present invention may continue with placing the cellulose in a closed container and decreasing the temperature to below 0° C. After a period of time, the temperature is increased to above freezing and excess moisture that is released from the cellulose is removed. This results in partially dehydrated cellulose. Without being bound to any one theory, it is believed that at below 0° C., water crystals form and are brought to the surface of the cellulose mesh. At above freezing temperature the liquid that has been removed is not allowed to rehydrate the surgical mesh, thereby yielding a product having increased tensile strength, elongation (stretch), conformability and suture retention when used as an implantable medical device for various surgical procedures. Depending on the desired level of dehydration, the films are exposed to one or more temperature variation cycles. The excess liquid is removed by pouring, dabbing or vacuuming it off. The partially dehydrated material is packaged in a single- or double-pouch system in preparation for sterilization. Samples are tested for cellulose content, endotoxin (LAL) and mechanical strength.

Driving Using Supercritical Carbon Dioxide

Following the partial dehydration described above, the cellulose pellicle may be further dried by exchanging the liquid in the pad for an organic solvent followed by placing the pellicle under pressure in a supercritical carbon dioxide filled chamber. Once all of the organic solvent has been removed, the liquid $CO_2$ temperature is increased so that the $CO_2$ forms a gas that is then released. The result is a dried product that can undergo cutting, packaging and sterilization.

The following examples serve to illustrate the present invention. It is to be understood that the examples are not restrictive of the present invention.

EXAMPLE 1

Manufacture of Implantable Microbial-Derived Cellulose as an Onlay Dura Substitute This example is directed to a preparation of standard mechanically modified microbial-derived cellulose films produced by *A. xylinum* within a controlled environment to minimize bioburden (microorganism contamination.) From a propagation vessel, sterilized media was inoculated with *A. xylinum*, filled into bioreactor trays and incubated until optimal growth of the pellicle was observed. The pellicles were removed from the trays and then underwent caustic chemical processing (depyrogenation) in a tank for about one hour. The pellicles then underwent a continuous rinse with filtered water. The films were compressed within a pneumatic press to yield a pellicle having a weight of approximately 4 to 10 g. Each unit was placed in a pouch, sealed, sterilized and used for various tests, inclusive of cellulose content, endotoxin (LAL), and mechanical strength.

EXAMPLE 2

Manufacture of Implantable Microbial-Derived Cellulose as a Suturable Dura Substitute This example is directed to a preparation of standard thermally modified microbial cellulose films per the initial steps of Example 1. Following chemical processing, the films were compressed within a pneumatic press to yield a pellicle having a weight of approximately 9 to 13 g. Each unit was placed in a closed container and decreased in temperature to below 0° C. After at least 24 hours, the temperature was increased to above freezing and excess moisture that was released was decanted to partially dehydrate the cellulose. The partially dehydrated material was placed in a pouch, sealed, sterilized and used for various tests, inclusive of cellulose content, endotoxin (LAL) and mechanical strength.

EXAMPLE 3

Physical Testing of the Dura Substitute

Cellulose sheets described in the previous example were tested with the following procedures:

(1) Cellulose Content

The cellulose content of material prepared by Examples 1 and 2 was evaluated to determine the cellulose content. Samples were cut to specific dimensions and weighed on an analytical balance. They were then dried in a 60° C. oven for 24 hours, after which they were again weighed. The dry weight was expressed as a percent of the wet weight to obtain the cellulose content. FIG. 1 illustrates the comparison in cellulose content for the MMMC and TMMC dura replacement materials.

(2) Suture Strength Testing

The artificial suturable dura mater substitute of the invention samples were cut into test pieces each having a size of 1 cm×4 cm. The test piece was penetrated with 5-0 nylon monofilament suture using a ½ circle taper point at 3 mm from the edge. Suture strength was measured by conducting a tensile test under the conditions of a gap distance of 6 cm and a crosshead speed of 300 mm/min. The average suture retention strength of the thermally modified cellulose was 1.48N (0.56 MPa), suitable and adequate for implant.

(3) Tensile Strength Testing

Figure 2:
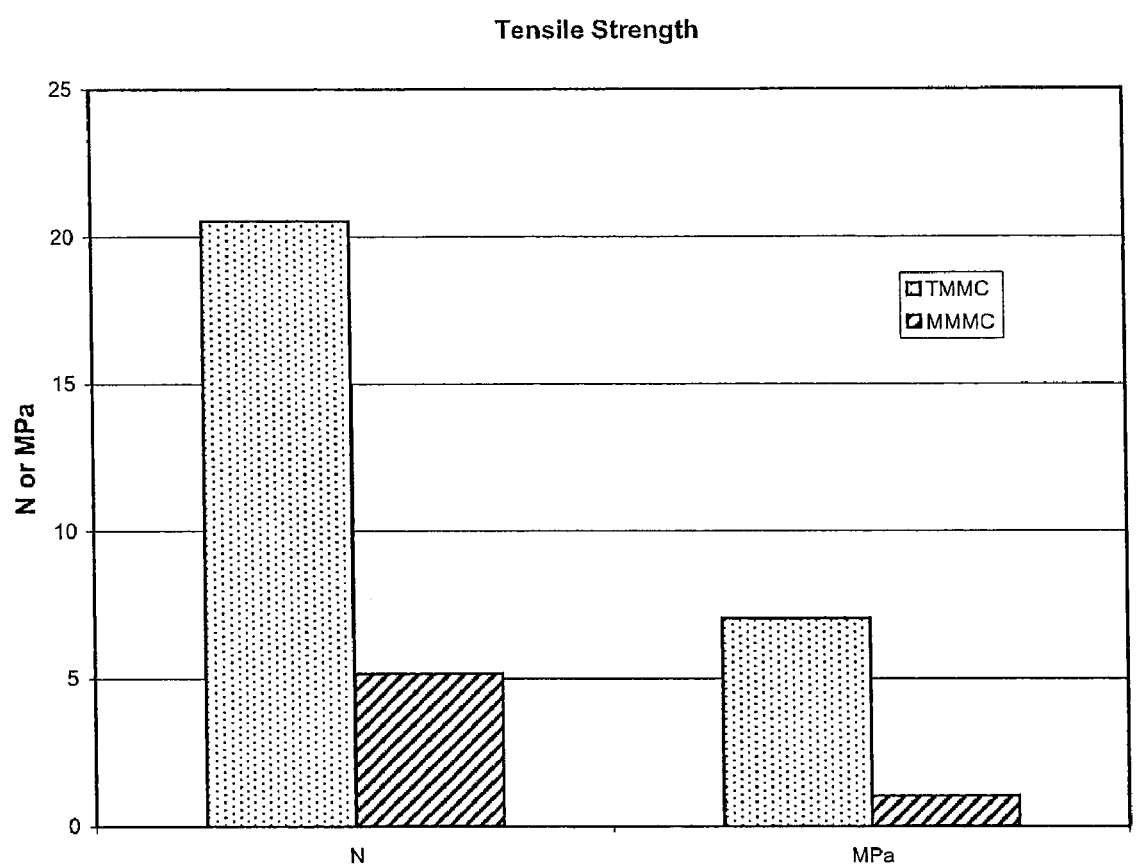
FIG. 2 shows mechanical strength (Force (N)) of the thermally modified microbial-derived cellulose (TMMC) compared to mechanically modified microbial cellulose (MMMC).
Figure 3:
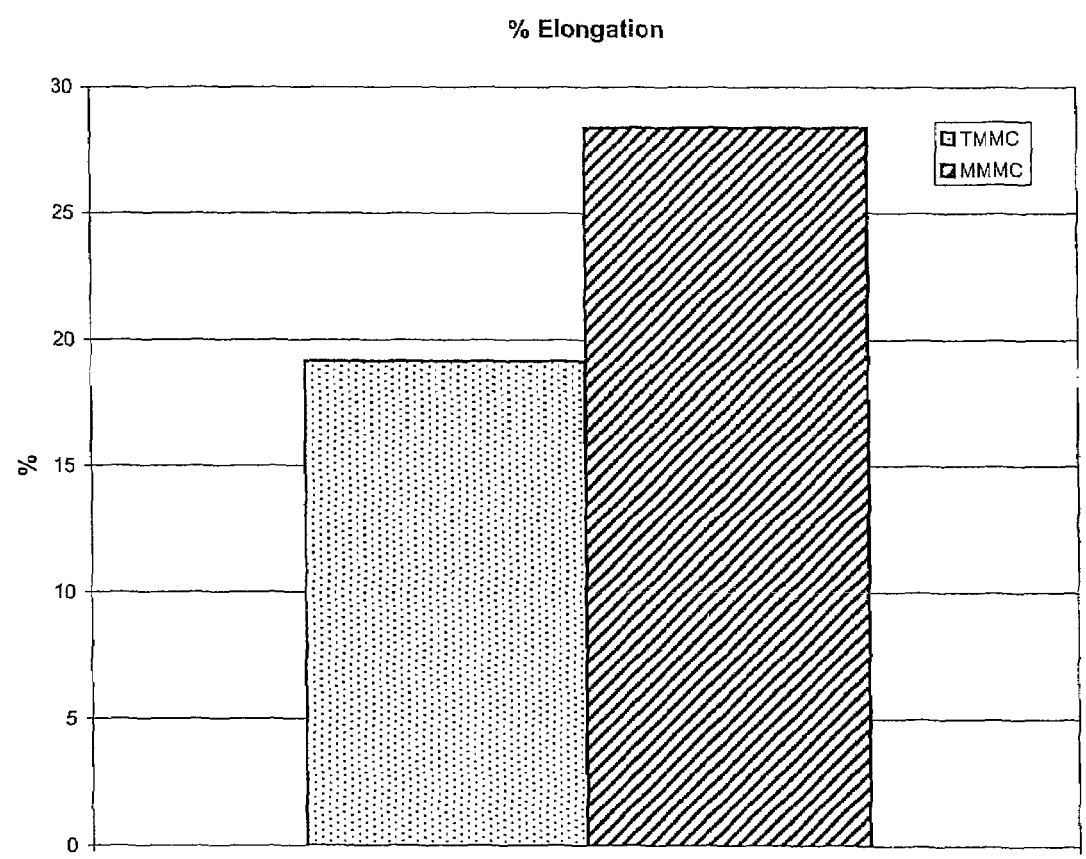
FIG. 3 shows elongation of thermally modified microbial-derived cellulose (TMMC) compared to mechanically modified microbial cellulose (MMMC).

The artificial onlay and suturable dura mater substitutes of the invention samples were cut into test pieces each having a size of 1 cm×4 cm. Tensile strength and % elongation were measured by conducting a standardized tensile test on a United Mechanical Testing Machine under the conditions of a gap distance of 2.5 cm and a crosshead speed of 300 mm/min. Results are presented in Table 1 and FIGS. 2 and 3. As expected, the suturable has higher tensile strength whereas the onlay demonstrates greater elongation.

TABLE 1

| Indication | Tensile (N) | Tensile (MPa) | % Elongation |
| --- | --- | --- | --- |
| Onlay (MMMC) | 5.16 ± 0.95 | 1.03 ± 0.29 | 28.41 ± 5.16 |
| Suturable (TMMC) | 20.54 ± 8.52 | 7.05 ± 2.88 | 19.15 ± 5.89 |

(3) Thickness

The artificial dura mater of the invention samples were measured for initial thickness using a caliper with an error of 0.03 mm. Average thickness of the samples is presented in Table 2. As expected, the suturable is thinner due to the effect of the thermal modification.

TABLE 2

| Indication | Thickness (mm) |
| --- | --- |
| Onlay (MMMC) | 0.58 ± 0.11 |
| Suturable (TMMC) | 0.31 ± 0.09 |

EXAMPLE 4

Dura Substitute Evaluation in Rabbits

An experimental study was conducted at the North American Science Associates (NAmSA) in Northwood, Ohio to evaluate the local tissue reaction of the dura substitute test articles in contact with dura and brain tissue. Two microbial cellulose materials were under investigation in this study, the thermally modified (TMMC) and the mechanically modified (MMMC). Both materials are intended as dura substitutes, the TMMC as a suturable material and the MMMC as an onlay.

Eight rabbits divided into two groups were studied. Once the rabbits were anesthetized, a dorsal, midline incision was created in the skin on the head between the sagittal crest and a point on the midline approximately 2 cm caudal to the eye orbits. The fascia and muscle were exposed and a 1.5 cm×1.5 cm defect was created in the skull using a high speed surgical handpiece with an appropriate bur. The defect was properly irrigated to remove any bone chips from the area and an approximate 1 cm×1 cm durotomy was then created. The appropriate test article was inserted under the border of the dural defect of the designated animals. Four animals received the thermally modified dura substitute and four received the mechanically modified dura substitute. The tissues were approximated and closed with the appropriate sutures and the animals were returned to their cage for monitoring and post operative care.

Animals were sacrificed at 14 days post-operative and were evaluated for: adhesions, cerebral spinal fluid (CSF) leakage, implant anchorage, device vascularization, infection, hydrocephalus and hemorrhage. A microscopic evaluation was performed to determine foreign body reactions. Results of these implantation studies performed at NAmSA have shown that the two materials described in this invention have performed well as dura substitutes. The implants were well tolerated by the animals and minimal adhesions were observed. In addition, there was no incidence of infection, hydrocephalus or hemorrhage at the implant site. The dura substitutes also no leakage of CSF for both onlay and sutureable versions.

EXAMPLE 5

Physician Evaluation of Material Characteristics

A group of neurosurgeons were gathered to evaluate the dura substitute material presented in this invention. The group was at first interviewed to determine those product characteristics that they felt were the most critical for a successful dura replacement material. Those characteristics were ranked as follows:

1—Lack of foreign body reactions
2—Lack of latent disease transmission.
2—Ease of handling—drapes and conforms to contours well; elasticity
3—Ready to use, minimal preparation time
4—Lack of swelling
4—Ability to maintain fluid balance
5—Lack of adhesions
5—On-lay, self sealing ability
6—Cellular matrix development: promotes dural regeneration.
7—Cellular matrix development: cell occlusive
8—Resorbability Neurosurgeons were then given various prototypes of dura substitute material and were asked to evaluate each prototype according to the following criteria. A hands-on workstation was provided for each prototype to be evaluated in terms of the following;
 a) Sutureability
 b) Flexibility/conformability
 c) Elasticity
 d) Thickness
 e) Packaging/readiness to use Based on the subjective scores assigned to each prototype by the surgeon evaluators, their first choice were the two materials described in this invention, namely 1) the partially thermally modified microbial cellulose and 2) the microbial cellulose that was partially dehydrated by mechanical means.

The present invention is further illustrated by, though in no way limited to, the following numbered embodiments. It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents. All patents, publications and references cited herein are expressly incorporated herein by reference in their entireties to the same extent as if individually incorporated by reference.

We claim:

1. A method for producing a dural substitute, comprising:
 (a) producing a cellulosic material from a culture of *Acetobacter xylinum*;
 (b) removing contaminants from the cellulosic material by contacting the cellulosic material with a caustic solution and subsequently contacting the cellulosic material with water to rinse said cellulosic material; and
 (c) removing at least a portion of the water from the cellulosic material by:
  (i) freezing moisture in the cellulosic material;
  (ii) melting at least a portion of the frozen moisture; and
  (iii) removing at least a portion of the melted moisture from said cellulosic material,
 thereby providing a cellulosic dural substitute which is a cellulosic sheet, mesh, or film.

2. The method of claim 1, wherein the cellulosic material is produced by fermentation.

3. The method of claim 2, wherein the fermentation occurs under static conditions and progresses for about 5 to about 30 days.

4. The method of claim 1, wherein removing contaminants from the cellulosic material renders the cellulosic material non-pyrogenic.

5. The method of claim 4, wherein the non-pyrogenic, cellulosic material is placed within a container prior to the freezing step.

6. The method of claim 5, wherein the removed melted moisture is removed from the container.

7. The method of claim 1, wherein the cellulosic material is further processed by:
 (d) exchanging the moisture in the cellulosic material with an organic solvent;

(e) exchanging the organic solvent with a supercritical fluid; and
(f) removing the supercritical fluid as a gas.

8. A method for producing a dural substitute, comprising:
(a) producing a cellulosic material by fermenting a culture of *Acetobacter xylinum;*
(b) removing contaminants from the cellulosic material by contacting the cellulosic material with a caustic solution and subsequently contacting the cellulosic material with water to rinse said cellulosic material; and
(c) removing at least a portion of the water from the cellulosic material by
   (i) processing the cellulosic material at a temperature below 0° C. to freeze the water associated with the cellulosic material;
   (ii) melting at least a portion of the frozen water associated with the cellulosic material; and
   (iii) removing at least a portion of the melted water from said cellulosic material,
thereby providing a cellulosic dural substitute which is a cellulosic sheet, mesh, or film.

9. The method of claim 8, wherein the fermentating occurs under static conditions and progresses for about 5 to about 30 days.

10. The method of claim 8, wherein removing contaminants from the cellulosic material renders the cellulosic material non-pyrogenic.

11. The method of claim 10, wherein the non-pyrogenic, cellulosic material is placed within a container prior to the freezing step.

12. The method of claim 11, wherein the removed melted water is removed from the container.

13. The method of claim 8, wherein the cellulosic material is further processed by:
(d) exchanging the moisture in the cellulosic material with an organic solvent;
(e) exchanging the organic solvent with a supercritical fluid; and,
(f) removing the supercritical fluid as a gas.

* * * * *